(12) United States Patent
Kakileti et al.

(10) Patent No.: US 12,324,677 B2
(45) Date of Patent: Jun. 10, 2025

(54) SYSTEM AND METHOD FOR QUANTITATIVE EVALUATION OF BREAST HEALTH

(71) Applicant: NIRAMAI HEALTH ANALYTIX PVT. LTD, Bangalore (IN)

(72) Inventors: Siva Teja Kakileti, Kakinada (IN); Geetha Manjunath, Bangalore (IN); V. N Ratna Kumari T, Hyderabad (IN); Kanchana Gopinath, Bangalore (IN); Himanshu J Madhu, Bangalore (IN)

(73) Assignee: NIRAMAI HEALTH ANALYTIX PVT. LTD, Bangalore (IN)

( * ) Notice: Subject to any disclaimer, the term of this patent is extended or adjusted under 35 U.S.C. 154(b) by 297 days.

(21) Appl. No.: 18/009,303

(22) PCT Filed: Jun. 3, 2021

(86) PCT No.: PCT/IN2021/050539
§ 371 (c)(1),
(2) Date: Dec. 8, 2022

(87) PCT Pub. No.: WO2021/250693
PCT Pub. Date: Dec. 16, 2021

(65) Prior Publication Data
US 2024/0000372 A1     Jan. 4, 2024

(30) Foreign Application Priority Data
Jun. 9, 2020   (IN) .............................. 202041024230

(51) Int. Cl.
*G06K 9/00*     (2022.01)
*A61B 5/00*     (2006.01)
(Continued)

(52) U.S. Cl.
CPC ............ *A61B 5/4312* (2013.01); *A61B 5/015* (2013.01); *A61B 5/7264* (2013.01);
(Continued)

(58) Field of Classification Search
CPC .......... A61K 35/12; G06K 9/00; G16H 30/20; A61B 5/00
(Continued)

(56) References Cited

U.S. PATENT DOCUMENTS

| | | | |
|---|---|---|---|
| 10,055,542 B2 * | 8/2018 | Venkataramani | G16H 50/30 |
| 2003/0055471 A1 * | 3/2003 | Fenn | A61N 5/02 607/101 |

(Continued)

OTHER PUBLICATIONS

Google search history (Year: 2019).*
(Continued)

*Primary Examiner* — Seyed H Azarian

(57) ABSTRACT

A system and method for a quantitative evaluation of a breast health of a pregnant and lactating woman for clinical management of a breast feeding by performing (i) receiving a thermal image of a breast region of the pregnant and lactating woman, (ii) automatically determine network structures associated with ductal or vascular thermal patterns of the pregnant and lactating woman by analysing the thermal images of the pregnant and lactating woman, (iii) estimate quantitative parameters corresponding to the network structures associated with the ductal or vascular thermal patterns using the machine learning model and (iv) generate a breast health report with the estimated quantitative parameters and the schematics of vascular network to enable clinical management of breastfeeding.

15 Claims, 7 Drawing Sheets

(51) Int. Cl.
  *A61B 5/01* (2006.01)
  *G06T 7/00* (2017.01)
  *G16H 10/60* (2018.01)
  *G16H 15/00* (2018.01)

(52) U.S. Cl.
  CPC .......... G06T 7/0012 (2013.01); G16H 10/60 (2018.01); G16H 15/00 (2018.01); *G06T 2207/10048* (2013.01); *G06T 2207/30068* (2013.01)

(58) Field of Classification Search
  USPC ....... 382/100, 103, 106, 128–133, 154, 156, 382/162, 168, 173, 181, 189.199, 219, 382/224, 254, 274, 276, 286–291, 305, 382/312; 607/101, 108, 96; 435/6.11
  See application file for complete search history.

(56) References Cited

U.S. PATENT DOCUMENTS

| | | | |
|---|---|---|---|
| 2011/0165566 A1* | 7/2011 | Wittliff | C12Q 1/6886 435/6.11 |
| 2015/0359665 A1* | 12/2015 | Vasconcellos | A61F 7/02 607/108 |
| 2017/0249738 A1* | 8/2017 | Sivakumar | G16H 30/20 |
| 2020/0297043 A1* | 9/2020 | Trangmar | A41C 5/00 |
| 2020/0324030 A1* | 10/2020 | Powell | A61M 1/062 |

OTHER PUBLICATIONS

Rev. Bras. Ginecol. Obstet. 40 (06) • Jun. 2018 • https://doi.org/10.1055/s-0038-1657766 Open-access Breastfeeding and the Benefits of Lactation for Women's Health (Year: 2018).*
Breastfeeding and the Benefits of Lactation for Women's Health (Year: 2019).*

* cited by examiner

THERMAL ANALYSIS

AEROLAR SYMMETRY: 0%
WARMSPOT SYMMETRY: 42%

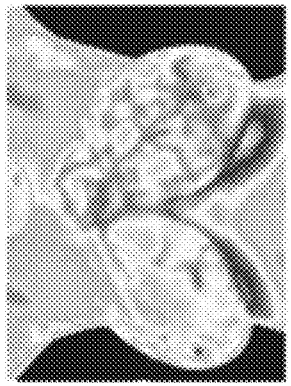

THERMAL SYMMETRY: 6%
VASCULAR SYMMETRY: 64%

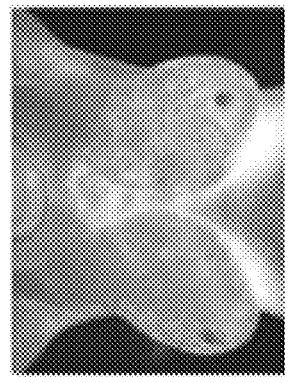

| THERMAL PARAMETERS | RIGHT BREAST | LEFT BREAST |
|---|---|---|
| NUMBER OF HOTSPOTS | 5 | 2 |
| EXTENT | HOT SPOTS SEEN IN 0.0738% OF REGION OF INTEREST | HOT SPOTS SEEN IN 0.2939% OF REGION OF INTEREST |
| HOTSPOT SHAPE | 1.02 IRREGULAR. 1667μ DISTORTED | 1.18 IRREGULAR. 2026μ DISTORTED |
| TEMPERATURE | 2.11°C INCREASE W.R.T SURROUNDING REGION | 1.97°C INCREASE W.R.T SURROUNDING REGION |
| AEROLAR HOTSPOT DETECTED | NONE | |
| LUMP | NONE | |
| VASCULAR PARAMETERS | BRANCHES: 15 VESSELS: 4 | BRANCHES: 16 VESSELS: 9 |

FIG. 4B

SYSTEM AND METHOD FOR QUANTITATIVE EVALUATION OF BREAST HEALTH

BACKGROUND

Technical Field

The present invention is directed toward breast health monitoring and, more particularly, to a system and method for a quantitative evaluation of breast health of a pregnant and lactating woman for clinical management of a breastfeeding.

Description of the Related Art

Breastfeeding significantly impacts the health of both mother & infant. Exclusive breastfeeding rates in India are as low as 54.9)%. Only half of the children in India are breastfed. World Health Organisation recommends exclusive breastfeeding for the first six months. Though all women initiate breastfeeding, many encounter problems that affect their ability to continue. The biggest fear a woman face is a perception of milk insufficiency, resulting in the early use of supplements. The earlier use of supplements leads to early weaning as using supplements affects milk production, and other reasons for early weaning include (i) Previous negative breastfeeding experience, (ii) Breast/nipple pain, (iii) Latching issues, and (iv) Lack of appropriate guidance.

Potential breast milk production in humans is higher than the average milk intake by the infants. The most widely used method for measuring milk intake by an infant test weighing, where the infant is weighed before and after each feeding. The breast milk production in humans is measured by a combination of test weighing and extraction of residual milk. These mechanical procedures are tedious. There are some breastfeeding assessment tools like breastfeeding assessment score (BAS) tool and breastfeeding attrition prediction tool (BAPT) from questionnaires to predict the risk of early weaning. These questionnaires include clinical parameters affecting breastfeeding, psychometric parameters affecting feeding, latching issues during feeding, and Infant suckling issues. But as they involve assessing only one aspect of breastfeeding issues (either clinical or psychometric), the assessment is not completed. Further, as questionnaire assessment is subjective and generic (not personalized) in nature, the prediction accuracy is not high, less reliable, and less sensitive. Hence, there is a need for an alternate solution that generates quantitative parameters for effective clinical management of breastfeeding from an imaging-based test.

Breast thermography captures the amount of heat radiating from the surface of the body and measures the temperature patterns and temperature distribution on the chest. Estrogen and Progesterone hormones during pregnancy lead to increased proliferative and vascular activity in breasts. Considerable blood flow is required through mammary vessels for milk production. During lactation, mammary development increases the skin temperature of the breast. There is also an increase in metabolic heat production due to increased milk production which is mainly an exothermic process. Therefore, it is possible to evaluate breast health for clinical management of breastfeeding from thermography. But the manual interpretation of these temperature readings is not trivial as it involves a visual analysis of more than a hundred thousand pixels and is subjective.

Accordingly, there is a need for a system and method for a quantitative evaluation of the breast health of a pregnant and lactating woman for clinical management of breastfeeding.

SUMMARY

In view of the foregoing, an embodiment herein provides a method for a quantitative evaluation of a breast health of a pregnant and lactating woman for clinical management of a breast feeding. The method includes (i) receiving a thermal image of a breast region of the pregnant and lactating woman captured by at least one of a thermal imaging camera, thermal sensor, or a wearable contact based thermal device, characterized in that, (ii) automatically determining network structures associated with ductal or vascular thermal patterns of the pregnant and lactating woman by analysing the thermal images of the pregnant and lactating woman, (iii) estimating quantitative parameters corresponding to the ductal or vascular thermal patterns from the determined network structures using the machine learning model, (iv) generating a breast health report with the estimated quantitative parameters and the schematics of vascular network to enable clinical management of breastfeeding. The thermal imaging device includes an array of sensors and a specialized processor. The array of sensors converts an infrared energy into electrical signals on a per-pixel basis. The specialized processor processes the detected temperature values into at least one block of pixels to generate the thermal image. The network structures are determined by (a) finding cylindrical structures in the thermal image of the pregnant and lactating woman using a machine learning model or image processing techniques, (b) creating a graphical network using branch points and endpoints as vertices and edges as an obtained skeleton. The graphical network includes schematics of the ductal and vascular network which represents the ductal or vascular thermal patterns.

In some embodiments, the method includes comparing the quantitative parameters of a left breast of the pregnant and lactating woman with a right breast of the pregnant and lactating woman to determine an asymmetry in the ductal and vascular network. The identified asymmetry is included in the breast health report.

In some embodiments, the method includes comparing the quantitative parameters for each breast is compared with the previous breast health report of same person to provide a longitudinal view across trimesters to identify early weaning of new mothers or a positive development of milk ducts in the pregnant and lactating woman.

In some embodiments, the asymmetry in the vascular network is used to provide a lactation guidance to new mothers.

In some embodiments, the method includes (i) receiving the thermal image of the breast region of the pregnant and lactating woman from at least one of a thermal imaging camera, thermal sensor or a wearable contact based thermal device, characterizing in that (ii) automatically determining thermally active regions in the breast region of the pregnant and lactating woman by analyzing the thermal image of the pregnant and lactating woman using the machine learning model, (iii) estimating quantitative parameters corresponding to the hotspot structures parameters using the machine learning model and (iv) generating the breast health report with the estimated quantitative parameters and the schematics of hotspot structures to enable the clinical management of breastfeeding. The thermal image represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color. The determination of the thermally active regions includes (a) identifying a temperature threshold (T) using temperature distribution represented in the received thermal image(s), (b) generating a hotspot structure by identifying the pixels which are higher than the temperature threshold (T) and (c) determining hotspot structure parameters and a schematics of the hotspot structure by analyzing shape and temperature parameters of the generated hotspot structures.

In some embodiments, the method includes determining an asymmetry by comparing the quantitative parameters of a left breast with a right breast of the pregnant and lactating woman. The determined asymmetry is included in the breast health report.

In some embodiments, the method includes comparing the quantitative parameters for each breast with the previous breast health report of same person to provide a longitudinal view across trimesters to identify early weaning of new mothers or positive development of milk ducts in the pregnant and lactating woman.

In some embodiments, the asymmetry in the hotspot structures is used to provide lactation guidance to new mothers.

In some aspects, a system for a quantitative evaluation of a breast health of a pregnant and lactating woman for clinical management of a breastfeeding. The system includes a storage device and a processor. The storage device stores a set of machine-readable instructions. The processor is configured to retrieve the machine-readable instructions from the storage device which, when executed by the processor, enable the processor to (i) receive a thermal image of a breast region of the pregnant and lactating woman, captured by a thermal imaging camera, thermal sensor or a wearable contact based thermal device, characterized in that, (ii) automatically determine network structures associated with ductal or vascular thermal patterns of the pregnant and lactating woman by analysing the thermal images of the pregnant and lactating woman, (iii) estimate quantitative parameters corresponding to the network structures associated with the ductal or vascular thermal patterns from the determined network structures using the machine learning model and (iv) generate a breast health report with the estimated quantitative parameters and the schematics of vascular network to enable clinical management of breastfeeding.

The thermal imaging camera includes an array of sensors and a specialized processor. The array of sensors converts an infrared energy into electrical signals on a per-pixel basis. The specialized processor processes the detected temperature values into at least one block of pixels to generate the thermal image. The network structures are determined by (a) finding cylindrical structures in the thermal image of the pregnant and lactating woman using a machine learning model or image processing techniques and (b) creating a graphical network using branch points and endpoints as vertices and edges as an obtained skeleton. The graphical network includes schematics of the ductal and vascular network which represents the ductal or vascular thermal patterns.

In some embodiments, the processor is configured to determine an asymmetry by comparing the quantitative parameters of a left breast with a right breast of the pregnant and lactating woman. The determined asymmetry is included in the breast health report.

In some embodiments, the processor is configured to compare the quantitative parameters for each breast is compared with the previous breast health report of same person to provide a longitudinal view across trimesters to identify early weaning of new mothers or a positive development of milk ducts in the pregnant and lactating woman.

In some embodiments, the asymmetry in the vascular network is used to provide a lactation guidance to new mothers.

In some embodiments, the processor is configured to (i) receive the thermal image of the breast region of the pregnant and lactating woman, which represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color, characterizing in that, (ii) automatically determine thermally active regions in the breast region of the pregnant and lactating woman by analyzing the thermal image of the pregnant and lactating woman using the machine learning model, (iii) estimate quantitative parameters corresponding to the hotspot structures parameters using the machine learning model and (iv) generate the breast health report with the estimated quantitative parameters and the schematics of hotspot structures to enable the clinical management of breastfeeding. The determination of thermally active regions includes (a) identifying a temperature threshold (T) using temperature distribution represented in the received thermal image(s), (b) generating a hotspot structure by identifying the pixels which are higher than the temperature threshold (T) and (c) determining hotspot structure parameters and a schematics of the hotspot structure by analyzing shape and temperature parameters of the generated hotspot structures.

In some aspects, there is provided one or more non-transitory computer-readable storage medium storing the one or more sequence of instructions, which when executed by one or more processors, causes to perform a method for a quantitative evaluation of a breast health of a pregnant and lactating woman for clinical management of a breast feeding. The method includes (i) receiving a thermal image of a breast region of the pregnant and lactating woman captured by at least one of a thermal imaging camera, thermal sensor, or a wearable contact based thermal device, characterized in that, (ii) automatically determining network structures associated with ductal or vascular thermal patterns of the pregnant and lactating woman by analysing the thermal images of the pregnant and lactating woman, (iii) estimating quantitative parameters corresponding to the ductal or vascular thermal patterns from the determined network structures using the machine learning model, (iv) generating a breast health report with the estimated quantitative parameters and the schematics of vascular network to enable clinical management of breastfeeding. The thermal imaging device includes an array of sensors and a specialized processor. The array of sensors converts an infrared energy into electrical signals on a per-pixel basis. The specialized processor processes the detected temperature values into at least one block of pixels to generate the thermal image. The network structures are determined by (a) finding cylindrical structures in the thermal image of the pregnant and lactating woman using a machine learning model or image processing techniques, (b) creating a graphical network using branch points and endpoints as vertices and edges as an obtained skeleton. The graphical network includes schematics of the ductal and vascular network which represents the ductal or vascular thermal patterns.

In some embodiments, the method includes comparing the quantitative parameters of a left breast of the pregnant and lactating woman with a right breast of the pregnant and lactating woman to determine an asymmetry in the ductal and vascular network. The identified asymmetry is included in the breast health report.

In some embodiments, the method includes comparing the quantitative parameters for each breast is compared with the previous breast health report of same person to provide a longitudinal view across trimesters to identify early weaning of new mothers or a positive development of milk ducts in the pregnant and lactating woman.

In some embodiments, the method includes (i) receiving the thermal image of the breast region of the pregnant and lactating woman from at least one of a thermal imaging camera, thermal sensor, or a wearable contact based thermal device, characterizing in that (ii) automatically determining thermally active regions in the breast region of the pregnant and lactating woman by analyzing the thermal image of the pregnant and lactating woman using the machine learning model, (iii) estimating quantitative parameters corresponding to the hotspot structures parameters using the machine learning model and (iv) generating the breast health report with the estimated quantitative parameters and the schematics of hotspot structures to enable the clinical management of breastfeeding. The thermal image represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color. The determination of the thermally active regions includes (a) identifying a temperature threshold (T) using temperature distribution represented in the received thermal image(s), (b) generating a hotspot structure by identifying the pixels which are higher than the temperature threshold (T) and (c) determining hotspot structure parameters and a schematics of the hotspot structure by analyzing shape and temperature parameters of the generated hotspot structures.

In some embodiments, the method includes determining an asymmetry by comparing the quantitative parameters of a left breast with a right breast of the pregnant and lactating woman. The determined asymmetry is included in the breast health report.

In some embodiments, the method includes comparing the quantitative parameters for each breast with the previous breast health report of same person to provide a longitudinal view across trimesters to identify early weaning of new mothers or positive development of milk ducts in the pregnant and lactating woman.

In some embodiments, the system analysing the breast heat patterns is the most reliable and personalized to the pregnant and lactating woman. In some embodiments, the report empowers a physician in providing personalized care to the pregnant and lactating woman by guiding and predicting the lactation milk capacity, early weaning risk, and need for early intervention. The system and method do not induce any external radiation and hence, it is completely safe for pregnant or lactating woman. It is non-contact and painless. The generated quantitative parameters include the thermal and vascular heat patterns in breasts may enable the user to (i) guide lactating the pregnant and lactating woman, on which side to feed more, provide lactation guidance, and (ii) detect any abnormalities. The generated parameters may use to perform longitudinal analysis of thermograms for studying lactation-related problems like early weaning etc.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 4B illustrates an exemplary report with the estimated quantitative parameters and the schematics of vascular network according to some embodiments herein;

DETAILED DESCRIPTION OF PREFERRED EMBODIMENTS

Figure 1:
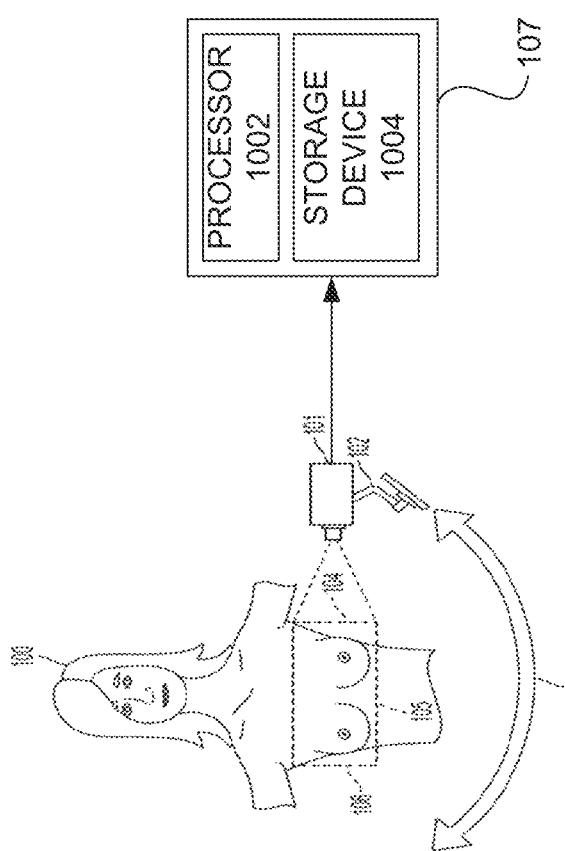
FIG. 1 illustrates a first exemplary environment diagram for a quantitative evaluation of a breast health of a woman for clinical management of a breast feeding according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and a method estimating the density of tissue from thermal images using a deep learning model for enabling a user to determine image modality. Referring now to the drawings, and more particularly to FIGS. 1 through 6, where similar reference characters denote corresponding features consistently throughout the figures, there are shown preferred embodiments.

A "person" and "subject" refer to a female. Gender pronouns are not to be viewed as limiting the scope of the appended claims strictly to females. Moreover, although the term "person" or "patient" or "subject" is used interchangeably throughout this disclosure, it should be appreciated that the person undergoing breast health screening may be something other than a human such as, for example, a primate. Therefore, the use of such terms is not to be viewed as limiting the scope of the appended claims to humans.

A "breast area" refers to a tissue of the breast and may further include surrounding tissue as is deemed appropriate for breast health screening. Thermal images are the capture of the breast area in various view angles which include a mediolateral view (center chest), a mediolateral oblique (angular) view, and a lateral (side) view, as are generally understood in the medical imaging arts. It should be appreciated that the mediolateral view is a supplementary mammographic view that generally shows less breast tissue and pectoral muscle than the mediolateral oblique view. FIG. 1 shows the breast area of a female 100. It should be appreciated that the patient may be stationary while the camera moves about the patient, or the patient can move while the camera remains stationary, or the patient and the camera may move to capture the appropriate view angles as desired.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colors that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are displayed in gradations of color between the first and second colors.

"Receiving a thermal image" of a patient for breast health screening is intended to be widely construed and includes retrieving, capturing, acquiring, or otherwise obtaining video image frames.

"Analysing the thermographic image" means to identify a plurality of points (PN) in the image.

FIG. 1 illustrates a first exemplary environment diagram for a quantitative evaluation of a breast health of a woman for clinical management of a breast feeding according to an embodiment herein. The thermal imaging camera 101 is mounted on a slidable and axially rotatable robotic arm 102 capable of moving the thermal imaging camera 101 along a semi-circular trajectory 103 in the front of the patient/subject from side-to-side such that thermographic images may be captured in a right-side view 104, a front view 105, and a left-side view 106, and various oblique angles in between. The thermal imaging camera 101 can be a single-band infrared camera, a multi-band infrared camera in the thermal range, or a hyperspectral infrared camera in the thermal range. The resolution of the thermal imaging camera 101 is effectively the size of the pixel. Smaller pixels mean that the resulting image has a higher resolution and thus better spatial definition. Although the thermal imaging camera 101 offers a relatively large dynamic range of temperature settings, it is preferable that a temperature range of the camera be relatively small and centered around a surface temperature of the body of the patient so that even small temperature variations are amplified in terms of pixel color changes in order to provide a better measure of temperature variation. Thermal imaging cameras are readily available in various streams of commerce. The thermal imaging camera 101 is communicatively connected to a quantitative evaluation system 107 which process the thermal image captured by the thermal imaging camera 101 for the quantitative evaluation of a breast health of a woman for clinical management of a breast feeding. In some embodiments, the quantitative evaluation system 107 includes a processor 1002 and a storage device 1004.

Figure 2:
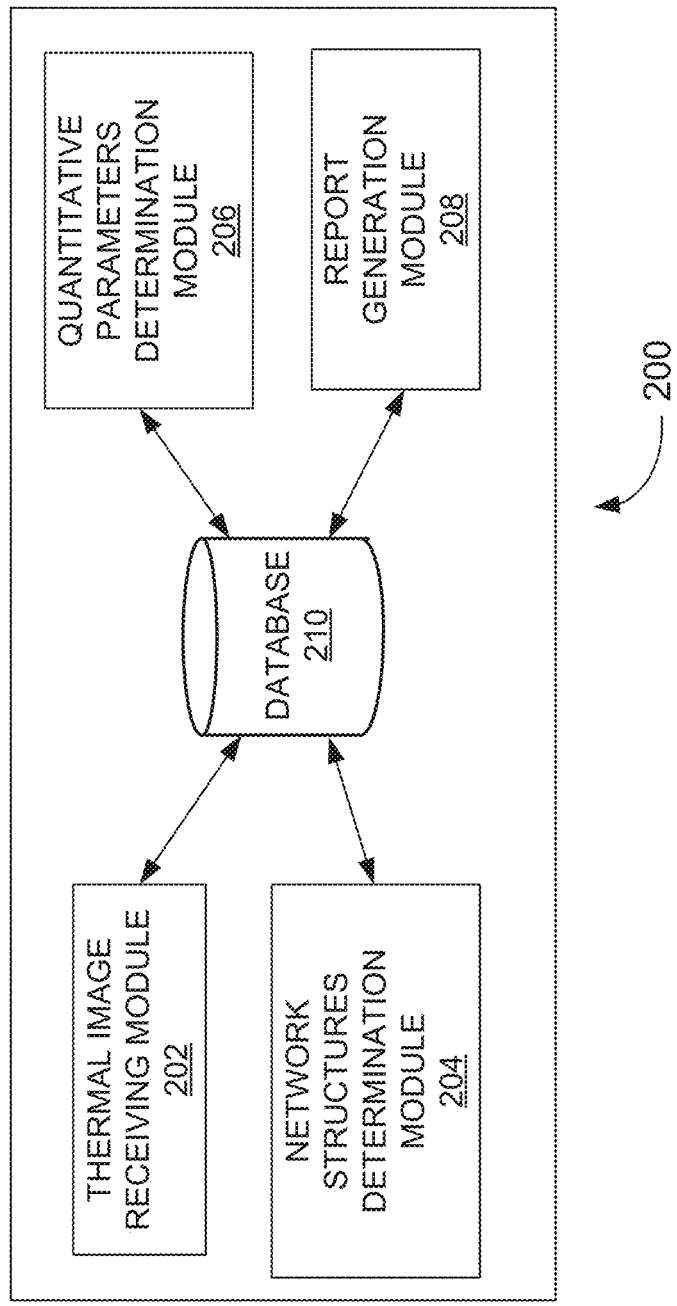
FIG. 2 illustrates an exploded view of a system for a quantitative evaluation of a breast health of a pregnant and lactating woman according to some embodiments herein.

FIG. 2 illustrates an exploded view of the quantitative evaluation system 107 for a quantitative evaluation of a breast health of a pregnant and lactating woman according to some embodiments herein. The block diagram 200 of the quantitative evaluation system 107 includes a thermal image receiving module 202, a network structures determination module 204, a quantitative parameters determination module 206, a text report generation module 208, and a database 210. The thermal image receiving module 202 receives a thermal image of a tissue of a pregnant and lactating woman. In some embodiments, the thermal image is captured using at least one of a thermal imaging camera 101 or a wearable device that is connected to the quantitative evaluation system 107. In some embodiments, the thermal imaging camera 101 or a wearable device includes an array of sensors, a lens, or a specialized processor. The array of sensors converts infrared energy into electrical signals on a per-pixel basis. The lens focuses the infrared energy from the tissue of the subject onto the array of sensors. The array of sensors detects temperature values from the tissue of the subject. The specialized processor processes the detected temperature values into at least one block of pixels to generate the thermal image. The network structures determination module 204 automatically determines network structures associated with ductal or vascular thermal patterns of the pregnant and lactating woman. The network structures determination module 204 analyses the thermal image of the pregnant and lactating woman using a machine learning model. In some embodiments, the network structures determination module 204 determines the network structures by performing (i) finding cylindrical structures in the thermal image of the pregnant and lactating woman using the machine learning model or image processing techniques and (ii) creating a graphical network using branch points and endpoints as vertices and edges as an obtained skeleton. In some embodiments, the graphical network includes schematics of the ductal and vascular network which represents the ductal or vascular thermal patterns. The quantitative parameters determination module 206 estimates quantitative parameters corresponding to the network structures associated with the ductal or vascular thermal patterns using the machine learning model. The text report generation module 208 generates a breast health report with the estimated quantitative parameters and the schematics of the vascular network. In some embodiments, the breast health report enables the clinical management of breastfeeding of the pregnant and lactating woman. The system 107 quantifies the heat patterns and vascularity in the breast to assess lactation milk capacity and any risk of early weaning. In some embodiments, the heat patterns may be captured and analysed using thermal infrared cameras. The quantitative evaluation system 107 enables the pregnant and lactating woman to perform proactive actions and supportive care for the establishment of breastfeeding, milk production, treatment, and prevention of diseases.

Figure 3:
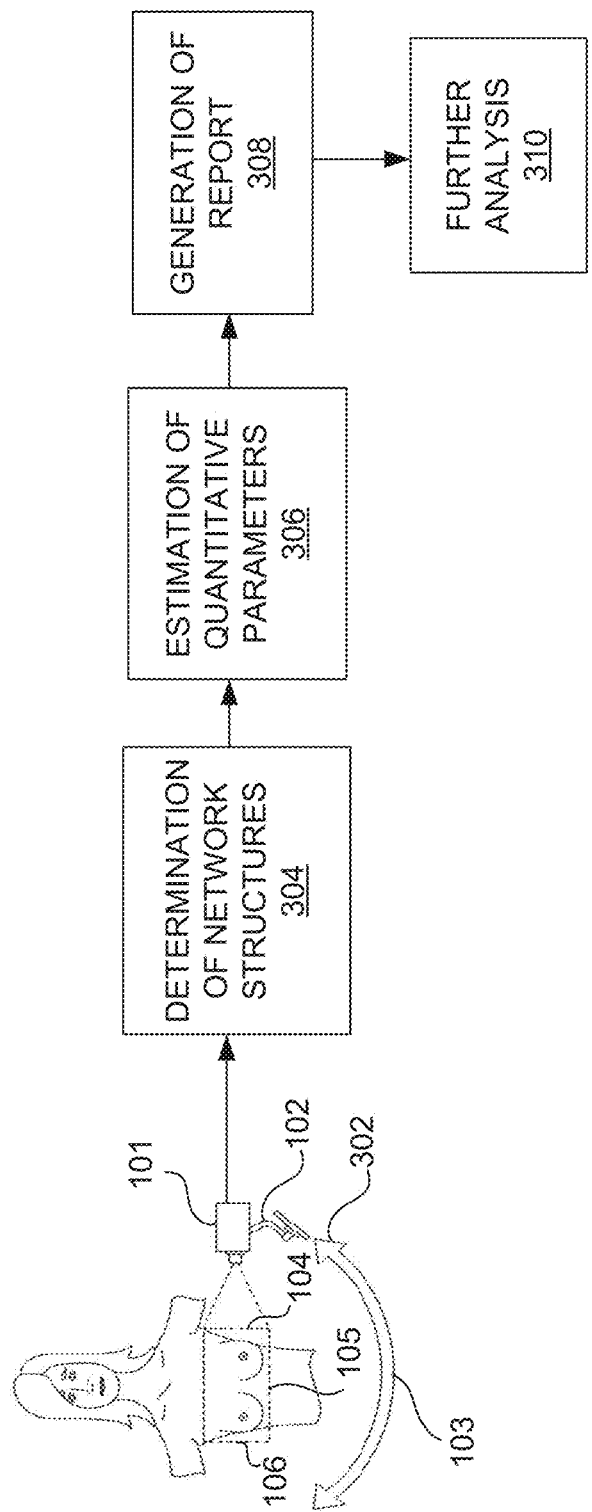
FIG. 3 illustrates an exemplary process flow of a quantitative evaluation of a breast health of a pregnant and lactating woman using quantitative parameters corresponding to ductal or vascular thermal patterns according to some embodiments herein.

With reference to FIGS. 2, FIG. 3 illustrates an exemplary process flow of a quantitative evaluation of a breast health of a pregnant and lactating woman using quantitative parameters corresponding to ductal or vascular thermal patterns according to some embodiments herein. At step 302, the thermal image is captured using a thermal imaging camera 101. In some embodiments, the thermal image may be received or retrieved from a remote device over a network, or from a media such as a Compact Disc Read-Only Memory (CDROM) or Digital Versatile/Video Disc (DVD). The thermal image may be downloaded from a web-based system or an application that makes a video available for processing, in accordance with the methods disclosed herein. The thermal image may also be received from an application such as applications available for handheld cellular devices and processed on the cell phone or other handheld computing devices such as an iPad or Tablet-PC. The thermal image may be received directly from a memory or storage device of the imaging device that is used to capture that thermal image or a thermal video. At step 304, the network structures associated with ductal or vascular thermal patterns of the pregnant and lactating woman are determined automatically by analysing the thermal images of the pregnant and lactating woman using the machine learning model. In some embodiments, the machine learning model finds the cylindrical structures in the thermal image of the pregnant and lactating woman. In some embodiments, the machine learning model creates a graphical network using branch points and endpoints as vertices and edges as an obtained skeleton. In some embodiments, the graphical network includes the schematics of the ductal and vascular network which represents the ductal or vascular thermal patterns. At step 306, the quantitative parameters corresponding to the ductal or vascular thermal patterns are estimated using the machine learning model. In some embodiments, the quantitative parameters include at least one of a number of edges corresponding to branches of vessels or ducts, a number of networks corresponding to ductal or vascular networks, edge length or diameter of the ductal or vascular networks, a symmetry of vessels or ducts between both breasts and temperature increases in the breasts. At step 308, the breast health report is generated with the estimated quantitative parameters and the schematics of the vascular network for further analysis 310.

Figure 4A:
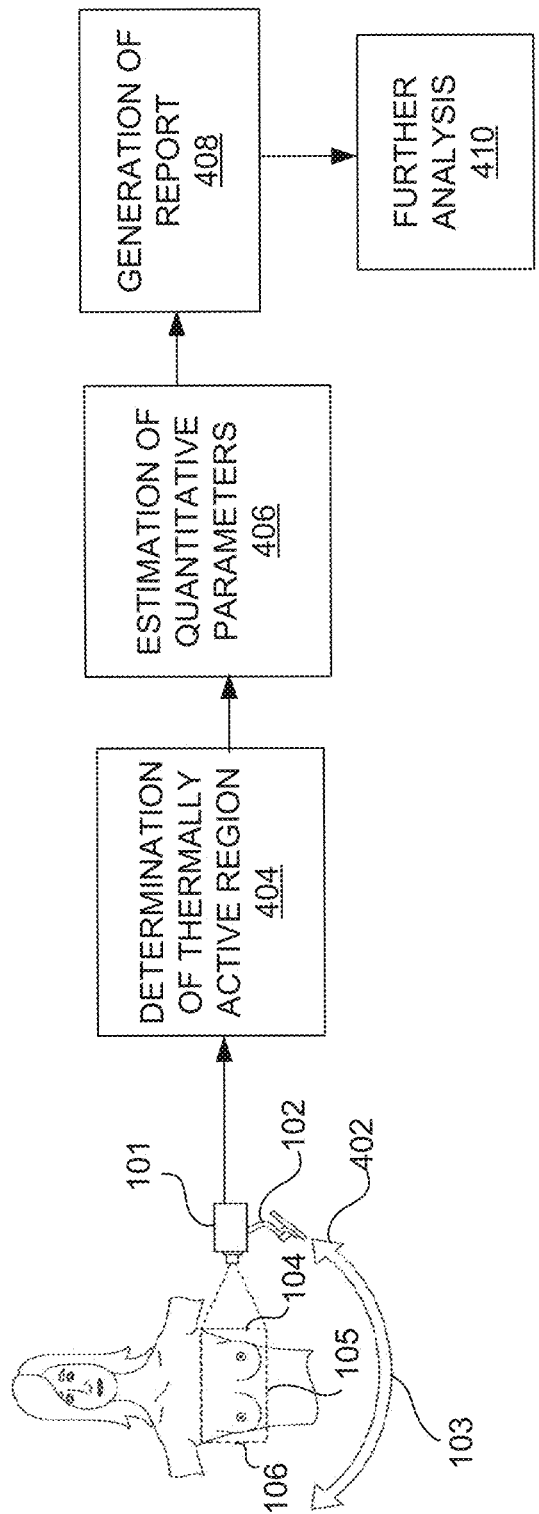
FIG. 4A illustrates an exemplary process flow of a quantitative evaluation of a breast health of a pregnant and lactating woman using quantitative parameters corresponding to hotspot structures parameters according to some embodiments herein.

With reference to FIG. 2, FIG. 4A illustrates an exemplary process flow of a quantitative evaluation of a breast health of a pregnant and lactating woman using quantitative parameters corresponding to hotspot structures parameters according to some embodiments herein. At step 402, the thermal image of the breast region of the pregnant and lactating woman is received from at least one of the thermal imaging camera 101, thermal sensor, or a wearable contact-based thermal device. In some embodiments, the thermal image represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color. At step 404, the machine learning model automatically determines thermally active regions in the breast region of the pregnant and lactating woman by analyzing the thermal image of the pregnant and lactating woman. In some embodiments, the machine learning model determines the thermally active regions by performing (i) an identification of a temperature threshold (T) using temperature distribution represented in the received thermal image(s). (ii) generation of a hotspot structure by identifying the pixels which are higher than the temperature threshold (T) and (iii) determining hotspot structure parameters and a schematics of the hotspot structure by analyzing shape and temperature parameters of the generated hotspot structures. At step 406, the quantitative parameters corresponding to the hotspot structures parameters are estimated using the machine learning model. At step 408, the breast health report is generated with the estimated quantitative parameters and the schematics of hotspot structures for further analysis 410.

With reference to FIG. 2, FIG. 4B illustrates an exemplary report with the estimated quantitative parameters and the schematics of the vascular network according to some embodiments herein. The report includes a status of the parameters such as at least one of number of hotspots, an extent, a hotspot shape, temperature, detected areolar hotspots, a lump, or vascular parameters. In some embodiments, the report includes the status of parameters associated with at least one of a left breast or a right breast.

Figure 5:
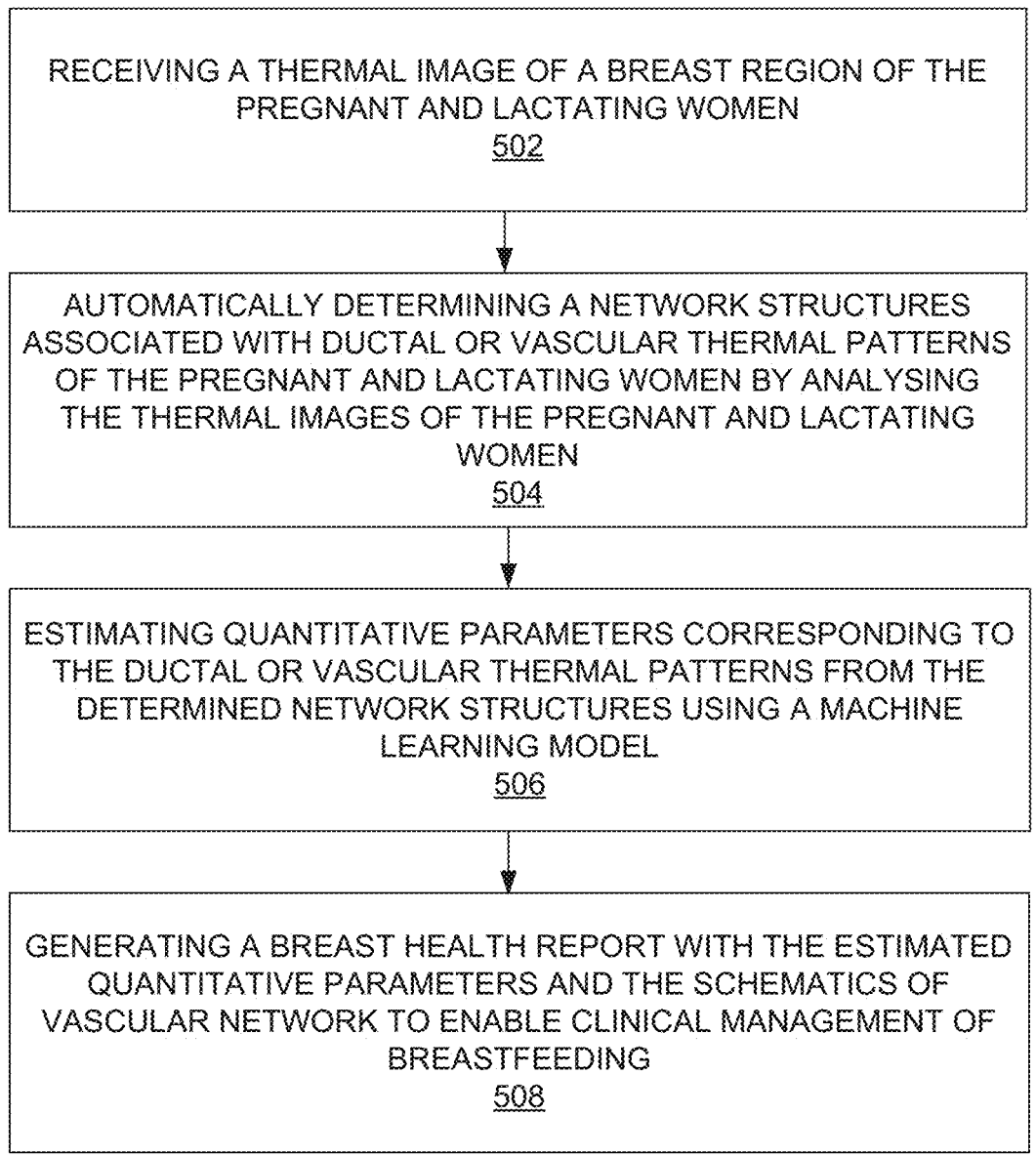
FIG. 5 illustrates a flow diagram of one embodiment of the present method for a quantitative evaluation of a breast health of a pregnant and lactating woman according to some embodiments herein.

With reference to FIG. 2, FIG. 5 illustrates a flow diagram of one embodiment of the present method for a quantitative evaluation of a breast health of a pregnant and lactating woman according to some embodiments herein. At step 502, the thermal image of the breast region of the pregnant and lactating woman is received. In some embodiments, the thermal image is captured by at least one of a thermal imaging camera, thermal sensor, or a wearable contact-based thermal device. At step 504, the network structures associated with the ductal or vascular patterns of the pregnant or lactating woman are determined by analysing the thermal images of the pregnant and lactating woman. In some embodiments, the network structures are determined by (i) finding the cylindrical structures in the thermal image of the pregnant and lactating woman using the machine learning model or the image processing techniques and (ii) creating a graphical network using the branch points and the endpoints as the vertices and the edges as an obtained skeleton. In some embodiments, the graphical network includes the schematics of the ductal and vascular network which represents the ductal or vascular thermal patterns. At step 506, the quantitative parameters corresponding to the ductal or vascular thermal patterns are estimated using the machine learning model. At step 508, the breast health report is generated with the estimated quantitative parameters and the schematics of the vascular network to enable clinical management of breastfeeding for the pregnant and lactating woman.

Figure 6:
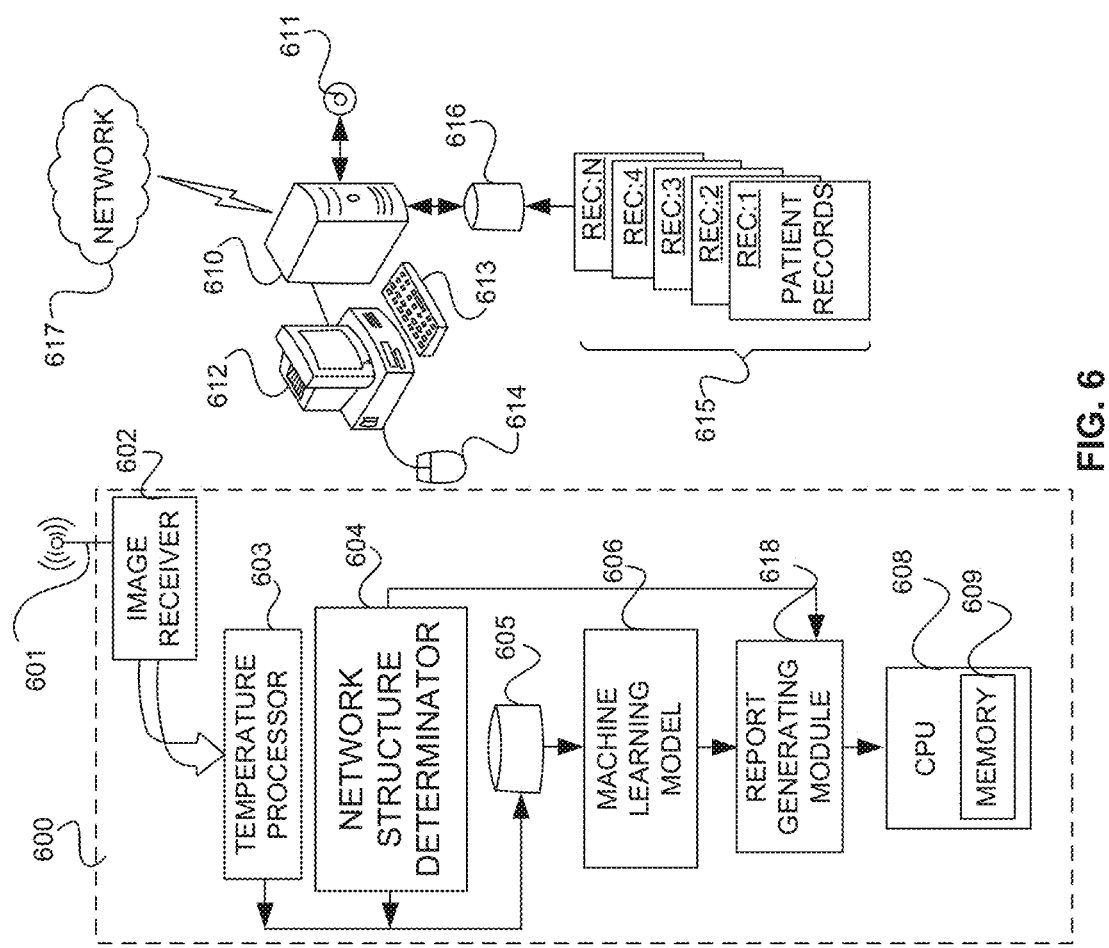
FIG. 6 illustrates a block diagram of one example system for processing a thermal image in accordance with the embodiments described with respect to the flow diagram of FIG. 5 according to some embodiments herein.

FIG. 6 illustrates a block diagram of one example system for processing a thermal image in accordance with the embodiments described with respect to the flow diagram of FIG. 5 according to some embodiments herein. The system includes an image receiver 602, a temperature processor 603, a density classifier 604, a storage device 605, a machine learning model 606, a Central Processing Unit (CPU) 608, a memory 609, a work station 610, a machine-readable media 611, a display device 612, a keyboard 613, a mouse 614, a database 616 and a network 617. In some embodiments, the Central Processing Unit (CPU) 608, the memory 60), the work station 610, the machine-readable media 611, the display device 612, the keyboard 613, the mouse 614, and the database 616 are connected to the system using the network 617. In some embodiments, the image receiver 602 wirelessly receives a video via antenna 601 having been transmitted thereto from the video/thermal imaging device 101 of FIG. 1. The temperate Processor 603 uses a temperature-based method to detect pixels in the received image. The network structures determinator 604 determines at least one of the network structures associated with ductal or vascular thermal patterns or thermally active regions in the breast region of the pregnant and lactating woman from the captured thermal image. Both the temperature processor 603 and the network structure determinator 604 store their results to the storage device 605. The machine learning model 606 retrieves the results from the storage device 605 and proceeds to evaluate a breast health of a pregnant and lactating woman for clinical management of a breast feeding. The machine learning model 606 estimates quantitative parameters corresponding to the ductal or vascular thermal. The machine learning model 606 is trained using a plurality of existing thermal images of pregnant and lactating woman and its corresponding estimated quantitative parameters and the schematics of vascular network as training data. The Central Processing Unit (CPU) 608 retrieves machine-readable program instructions from the memory 609 and is provided to facilitate the functionality of any of the modules of the system 600. The Central Processing Unit (CPU) 608, operating alone or in conjunction with other processors, may be configured to assist or otherwise perform the functionality of any of the modules or processing units of the system 600 as well as facilitate communication between the system 600 and the workstation 610.

The computer case of the workstation 610 houses various components such as a motherboard with a processor and a memory, a network card, a video card, a hard drive capable of reading/writing to machine-readable media 611 such as a floppy disk, optical disk, CD-ROM, DVD, magnetic tape, and the like, and other software and hardware needed to perform the functionality of a computer workstation. The workstation 610 further includes the display device 612, such as a CRT, LCD, or touch screen device, for displaying information, images, view angles, and the like. A user can view any of that information and make a selection from the menu options displayed thereon. The keyboard 613 and the mouse 614 effectuate a user input. It should be appreciated that the workstation 610 has an operating system and other specialized software configured to display alphanumeric values, menus, scroll bars, dials, slidable bars, pull-down options, selectable buttons, and the like, for entering, selecting, modifying, and accepting information needed for processing in accordance with the teachings hereof. The workstation 610 is further enabled to display thermal images, the view angle of the thermal images and the like as they are derived. A user or technician may use the user interface of the workstation 610 to set parameters and adjust various aspects of the determination of network structures, estimation of quantitative parameters and generation of the breast health report, as needed or as desired, depending on the implementation. Any of these selections or inputs may be stored/retrieved to the storage device 611. Default settings can be retrieved from the storage device 611. A user of the workstation 610 is also able to view or manipulate any of the data in the patient records, collectively at 615, stored in the database 616. Any of the received images, results, determined view angle, and the like, may be stored in the storage device 611 internal to the workstation 610. Although shown as a desktop computer, the workstation 610 can be a laptop, mainframe, or a special purpose computer such as an ASIC, circuit, or the like.

Any of the components of the workstation 610 may be placed in communication with any of the modules and processing units of system 600. Any of the modules of the system 600 can be placed in communication with the storage devices 605, 616, and 606 and/or the computer-readable media 611 and may store/retrieve therefrom data, variables, records, parameters, functions, and/or machine-readable/executable program instructions, as needed to perform their intended functions. Each of the modules of the system 600 may be placed in communication with one or more remote devices over the network 617. It should be appreciated that some or all of the functionality performed by any of the modules or processing units of the system 600 can be performed, in whole or in part, by the workstation 610. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

What is claimed is:

1. A method for a quantitative evaluation of a breast health of a woman for clinical management of a breastfeeding, the method comprising:

receiving a thermal image of a breast region of the woman captured by at least one of a thermal imaging camera, thermal sensor, or a wearable contact-based thermal device, the thermal imaging device comprising:

an array of sensors that converts an infrared energy into electrical signals on a per-pixel basis; and a specialized processor that processes the detected temperature values into at least one block of pixels to generate the thermal image;

characterized in that, automatically determining network structures associated with ductal or vascular thermal patterns of the woman by analysing the thermal images of the woman, wherein the network structures are determined by:

finding cylindrical structures in the thermal image of the woman using a machine learning model or image processing techniques; and creating a graphical network using branch points and endpoints as vertices and edges as an obtained skeleton, wherein the graphical network comprises schematics of the ductal and vascular network which represents the ductal or vascular thermal patterns;

estimating quantitative parameters corresponding to the ductal or vascular thermal patterns from the determined network structures using the machine learning model; and generating a breast health report with the estimated quantitative parameters and the schematics of vascular network to enable clinical management of breastfeeding, wherein the method comprises comparing the quantitative parameters of a left breast of a pregnant and lactating woman with a right breast of the pregnant and lactating woman to determine an asymmetry in the ductal and vascular network, wherein the identified asymmetry is included in the breast health report, wherein the asymmetry in the vascular network is used to provide a lactation guidance to new mothers.

2. The method of claim 1, wherein the method comprises comparing the quantitative parameters for each breast is compared with the previous breast health report of same person to provide a longitudinal view across trimesters to identify early weaning of new mothers or a positive development of milk ducts in a pregnant and lactating woman.

3. The method of claim 1, wherein the method comprises:

receiving the thermal image of the breast region of a pregnant and lactating woman from at least one of a thermal imaging camera, thermal sensor, or a wearable contact-based thermal device, wherein the thermal image represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color;

characterized in that, automatically determining thermally active regions in the breast region of the pregnant and lactating woman by analyzing the thermal image of the pregnant and lactating woman using the machine learning model, wherein said determination of the thermally active regions comprises;

identifying a temperature threshold (T) using temperature distribution represented in the received thermal image (s);

generating a hotspot structure by identifying the pixels which are higher than the temperature threshold (T); and determining hotspot structure parameters and a schematics of the hotspot structure by analyzing the shape and temperature parameters of the generated hotspot structures;

estimating quantitative parameters corresponding to the hotspot structures parameters using the machine learning model; and generating the breast health report with the estimated quantitative parameters and the schematics of hotspot structures to enable the clinical management of breastfeeding.

4. The method of claim 3, wherein the method comprises determining an asymmetry by comparing the quantitative parameters of a left breast with a right breast of the pregnant and lactating woman, wherein the determined asymmetry is included in the breast health report.

5. The method of claim 4, wherein the asymmetry in the hotspot structures is used to provide lactation guidance to new mothers.

6. The method of claim 3, wherein the method comprises comparing the quantitative parameters for each breast with the previous breast health report of same person to provide a longitudinal view across trimesters to identify early weaning of new mothers or positive development of milk ducts in the pregnant and lactating woman.

7. A system for a quantitative evaluation of a breast health of a pregnant and lactating woman for clinical management of a breastfeeding, the system comprising:

a storage device storing a set of machine-readable instructions; and a processor configured to retrieve the machine-readable instructions from the storage device which, when executed by the processor, enable the processor to:

receive a thermal image of a breast region of the pregnant and lactating woman, captured by a thermal imaging camera, thermal sensor or a wearable contact based thermal device, the thermal imaging camera comprising:

an array of sensors that converts an infrared energy into electrical signals on a per-pixel basis; and a specialized processor that processes the detected temperature values into at least one block of pixels to generate the thermal image;

characterized in that, automatically determine network structures associated with ductal or vascular thermal patterns of the pregnant and lactating woman by analysing the thermal images of the pregnant and lactating woman, wherein the network structures determined by:

finding cylindrical structures in the thermal image of the pregnant and lactating woman using a machine learning model or image processing techniques; and creating a graphical network using branch points and endpoints as vertices and edges as an obtained skeleton, wherein the graphical network comprises schematics of the ductal and vascular network which represents the ductal or vascular thermal patterns;

estimate quantitative parameters corresponding to the network structures associated with the ductal or vascular thermal patterns from the determined network structures using the machine learning model; and generate a breast health report with the estimated quantitative parameters and the schematics of vascular network to enable clinical management of breastfeeding, wherein the processor is configured to determine an asymmetry by comparing the quantitative parameters of a left breast of a pregnant and lactating woman with a right breast of the pregnant and lactating woman, wherein the determined asymmetry is included in the breast health report, wherein the asymmetry in the vascular network is used to provide a lactation guidance to new mothers.

8. The system of claim 7, wherein the processor is configured to determine an asymmetry by comparing the quantitative parameters of a left breast with a right breast of the pregnant and lactating woman, wherein the determined asymmetry is included in the breast health report.

9. The system of claim 8, wherein the processor is configured to receive the thermal image of the breast region of the pregnant and lactating woman, which represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color, characterizing in that, automatically determine thermally active regions in the breast region of the pregnant and lactating woman by analyzing the thermal image of the pregnant and lactating woman using the machine learning model, wherein said determination of thermally active regions comprises:
- identifying a temperature threshold (T) using temperature distribution represented in the received thermal image(s);
- generating a hotspot structure by identifying the pixels which are higher than the temperature threshold (T); and
- determining hotspot structure parameters and a schematics of the hotspot structure by analyzing shape and temperature parameters of the generated hotspot structures;

estimate quantitative parameters corresponding to the hotspot structures parameters using the machine learning model; and generate the breast health report with the estimated quantitative parameters and the schematics of hotspot structures to enable the clinical management of breastfeeding.

10. The system of claim 7, wherein the processor is configured to compare the quantitative parameters for each breast is compared with the previous breast health report of same person to provide a longitudinal view across trimesters to identify early weaning of new mothers or a positive development of milk ducts in the pregnant and lactating woman.

11. A non-transitory computer-readable storage medium storing the one or more sequence of instructions, which when executed by one or more processors, causes to perform a method for a quantitative evaluation of a breast health of a woman for clinical management of a breast feeding, by performing the steps of:
- receiving a thermal image of a breast region of the woman captured by at least one of a thermal imaging camera, thermal sensor or a wearable contact based thermal device, the thermal imaging device comprising:
- an array of sensors that converts an infrared energy into electrical signals on a per-pixel basis; and
- a specialized processor that processes the detected temperature values into at least one block of pixels to generate the thermal image;
characterized in that,
automatically determining network structures associated with ductal or vascular thermal patterns of the woman by analysing the thermal images of the woman, wherein the network structures determined by:
finding cylindrical structures in the thermal image of the woman using a machine learning model or image processing techniques; and
creating a graphical network using branch points and endpoints as vertices and edges as an obtained skeleton, wherein the graphical network comprises schematics of the ductal and vascular network which represents the ductal or vascular thermal patterns;
estimating quantitative parameters corresponding to the ductal or vascular thermal patterns from the determined network structures using the machine learning model; and generating a breast health report with the estimated quantitative parameters and the schematics of vascular network to enable clinical management of breastfeeding,
wherein the method comprises comparing the quantitative parameters of a left breast of a pregnant and lactating woman with a right breast of the pregnant and lactating woman to determine an asymmetry in the ductal and vascular network, wherein the identified asymmetry is included in the breast health report, wherein the asymmetry in the vascular network is used to provide a lactation guidance to new mothers.

12. The non-transitory computer-readable storage medium storing the one or more sequence of instructions of claim 11, wherein the method comprises comparing the quantitative parameters for each breast is compared with the previous breast health report of same person to provide a longitudinal view across trimesters to identify early weaning of new mothers or a positive development of milk ducts in a pregnant and lactating woman.

13. The non-transitory computer-readable storage medium storing the one or more sequence of instructions of claim 11, wherein the method comprises:
receiving the thermal image of the breast region of a pregnant and lactating woman from at least one of a thermal imaging camera, thermal sensor or a wearable contact based thermal device, wherein the thermal image represents the temperature distribution on the breast region of the pregnant and lactating woman as pixels in the thermal image with a highest temperature value being displayed in a first color and pixels with a lowest temperature value being displayed in a second color, pixels with temperature values between the lowest and highest temperature values being displayed in gradations of color between the first and second color;
characterizing in that
automatically determining thermally active regions in the breast region of the pregnant and lactating woman by analyzing the thermal image of the pregnant and lactating woman using the machine learning model, wherein said determination of the thermally active regions comprises;
identifying a temperature threshold (T) using temperature distribution represented in the received thermal image(s);
generating a hotspot structure by identifying the pixels which are higher than the temperature threshold (T); and
determining hotspot structure parameters and a schematics of the hotspot structure by analyzing shape and temperature parameters of the generated hotspot structures;
estimating quantitative parameters corresponding to the hotspot structures parameters using the machine learning model; and
generating the breast health report with the estimated quantitative parameters and the schematics of hotspot structures to enable the clinical management of breastfeeding.

14. The non-transitory computer-readable storage medium storing the one or more sequence of instructions of claim 13, wherein the method comprises determining an asymmetry by comparing the quantitative parameters of a left breast with a right breast of the pregnant and lactating woman, wherein the determined asymmetry is included in the breast health report.

15. The non-transitory computer-readable storage medium storing the one or more sequence of instructions of claim 13, wherein the method comprises comparing the quantitative parameters for each breast with the previous breast health report of same person to provide a longitudinal view across trimesters to identify early weaning of new mothers or positive development of milk ducts in the pregnant and lactating woman.

\* \* \* \* \*